US011096566B2

(12) United States Patent
Hagihara

(10) Patent No.: US 11,096,566 B2
(45) Date of Patent: Aug. 24, 2021

(54) ENDOSCOPE SYSTEM

(71) Applicant: OLYMPUS CORPORATION, Hachioji (JP)

(72) Inventor: Yoshio Hagihara, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 764 days.

(21) Appl. No.: 15/921,937

(22) Filed: Mar. 15, 2018

(65) Prior Publication Data
US 2018/0199802 A1 Jul. 19, 2018

Related U.S. Application Data

(63) Continuation of application No. PCT/JP2015/081596, filed on Nov. 10, 2015.

(51) Int. Cl.
A61B 1/05 (2006.01)
H04N 5/378 (2011.01)
A61B 1/00 (2006.01)
A61B 1/045 (2006.01)
G02B 23/24 (2006.01)
(Continued)

(52) U.S. Cl.
CPC .......... A61B 1/051 (2013.01); A61B 1/00018 (2013.01); A61B 1/00096 (2013.01); A61B 1/05 (2013.01); H04N 5/378 (2013.01); A61B 1/045 (2013.01); G02B 23/243 (2013.01); H04N 5/235 (2013.01); H04N 2005/2255 (2013.01)

(58) Field of Classification Search
CPC .............................. A61B 1/051; G02B 23/243
See application file for complete search history.

(56) References Cited

U.S. PATENT DOCUMENTS

2006/0238067 A1* 10/2006 Dausch ................ B06B 1/0622
310/311
2013/0331703 A1* 12/2013 Miyake ................ A61B 8/4494
600/459

FOREIGN PATENT DOCUMENTS

JP 7-184854 A 7/1995
JP 8-186850 A 7/1996
JP 2002-131656 A 5/2002
(Continued)

OTHER PUBLICATIONS

International Search Report dated Jan. 26, 2016, issued in counterpart International Application No. PCT/JP2015/081596, w/English translation (3 pages).

Primary Examiner — Alexandra L Newton
Assistant Examiner — Rynae Boler
(74) Attorney, Agent, or Firm — Westerman, Hattori, Daniels & Adrian, LLP

(57) ABSTRACT

An endoscope system includes an imaging element, a voltage-current conversion circuit, a first coaxial cable, and an impedance conversion circuit. The imaging element generates a first voltage. The voltage-current conversion circuit is disposed inside or outside the imaging element and converts the first voltage into a first current. The first coaxial cable has a first conductor and a second conductor. The second conductor is disposed outside the first conductor. The first current is transmitted through the first conductor. The first current transmitted through the first conductor is input to the impedance conversion circuit. The impedance conversion circuit outputs a second current according to the first current. A second voltage according to the first current is input to the second conductor.

3 Claims, 8 Drawing Sheets

(51) Int. Cl.
　　　*H04N 5/235* (2006.01)
　　　*H04N 5/225* (2006.01)

(56) References Cited

FOREIGN PATENT DOCUMENTS

JP　　　2010-523226 A　　7/2010
WO　　2008/124566 A2　10/2008

* cited by examiner

US 11,096,566 B2

ENDOSCOPE SYSTEM

This application is a continuation application based on International Patent Application No. PCT/JP2015/081596 filed on Nov. 10, 2015, the contents of which are incorporated herein by reference.

BACKGROUND OF THE INVENTION

Field of the Invention

The present invention relates to an endoscope system.

Description of Related Art

Endoscope devices having a scope are widely used. The scope has an elongated insertion portion. By inserting the insertion portion into a body cavity, a user can observe organs in the body cavity. Alternatively, by inserting a treatment tool into a treatment tool channel, the user can perform various treatment procedures. Also in industrial fields, industrial endoscope devices having a scope are widely used. By using an industrial endoscope device, a user can observe or inspect internal scratches and corrosion of a boiler, a turbine, an engine, a chemical plant and so on.

Generally, in a scope (electronic endoscope), a solid state imaging device as an imaging element is mounted at a distal end of the insertion portion. For example, the solid state imaging device is a charge coupled device (hereinafter, referred to as CCD). A signal line which transmits a driving signal for operating the CCD and a signal line which transmits an imaging signal from the CCD are disposed inside the insertion portion.

A scope (electronic endoscope) has a long insertion portion. A length of the signal line disposed inside the insertion portion is proportional to a length of the insertion portion. Therefore, the signal line may become long. When the signal line is long, the signal from the CCD is easily attenuated. To stabilize a waveform of the signal, a coaxial cable is generally used. The coaxial cable has a shield structure which prevents electrical interference and noise influence with respect to the signal. For example, the coaxial cable has a first conductor and a second conductor. The first conductor is disposed at the center of the coaxial cable. The second conductor covers the first conductor and is insulated from the first conductor.

In Japanese Unexamined Patent Application, First Publication No. H7-184854, an endoscope system is disclosed in which a bundle-shaped signal line is disposed. The bundle-shaped signal line includes a first signal line having a large diameter for preventing attenuation of a signal and a second signal line having a diameter different from that of the first signal line. Each of the signal lines is constituted with a coaxial cable.

SUMMARY OF THE INVENTION

According to a first aspect of the present invention, an endoscope system includes an imaging element, a voltage-current conversion circuit, a first coaxial cable, and an impedance conversion circuit. The imaging element generates a first voltage. The voltage-current conversion circuit is disposed inside or outside the imaging element and converts the first voltage into a first current. The first coaxial cable has a first conductor and a second conductor. The second conductor is disposed outside the first conductor. The first current is transmitted through the first conductor. The first current transmitted through the first conductor is input to the impedance conversion circuit. The impedance conversion circuit outputs a second current according to the first current. A second voltage according to the first current is input to the second conductor.

According to a second aspect of the present invention, in the first aspect, the endoscope system may further include a buffer configured to output the second voltage according to the first current.

According to a third aspect of the present invention, in the first aspect, the endoscope system may further include a second coaxial cable configured to transmit a power source voltage supplied to the imaging element.

According to a fourth aspect of the present invention, in the first aspect, the endoscope system may further include a current-voltage conversion circuit and a circuit board. The current-voltage conversion circuit may convert the second current output from the impedance conversion circuit into a third voltage. The impedance conversion circuit and the current-voltage conversion circuit may be disposed on the circuit board. The circuit board may include a first terminal and a second terminal. The first current transmitted through the first conductor may be input to the first terminal. The first terminal may be electrically connected to the impedance conversion circuit. The second terminal may be electrically connected to the impedance conversion circuit and may output the second voltage.

DETAILED DESCRIPTION OF THE INVENTION

Exemplary embodiments of the present invention will be described with reference to the drawings.

First Embodiment

Figure 1:
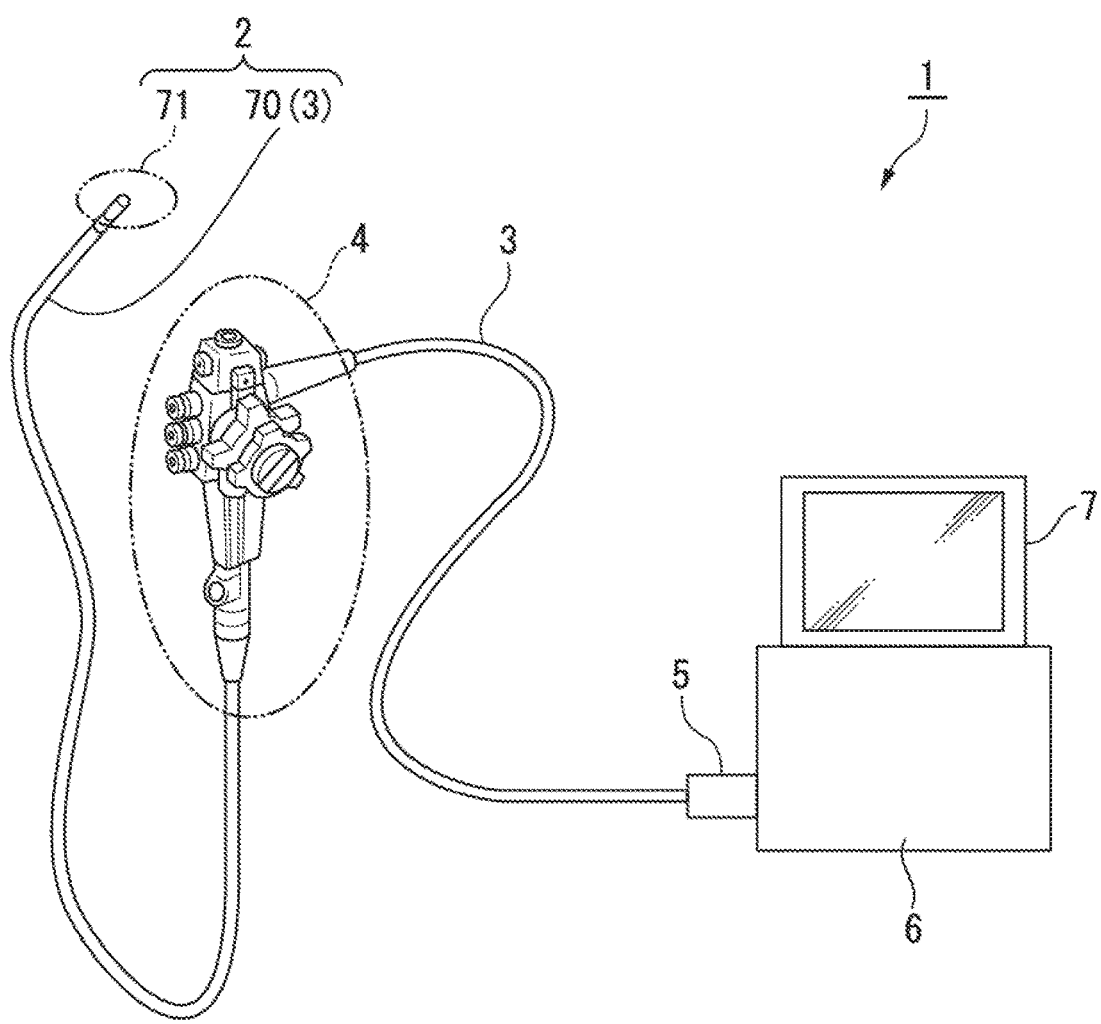
FIG. 1 is a schematic view showing a constitution of an endoscope system according to a first embodiment of the present invention.

FIG. 1 is a schematic view showing a constitution of an endoscope system 1 according to a first embodiment of the present invention. As shown in FIG. 1, the endoscope system 1 includes a scope 2, a transmission cable 3, an operation unit 4, a connector unit 5, a processor 6, and a display device 7.

Figure 2:
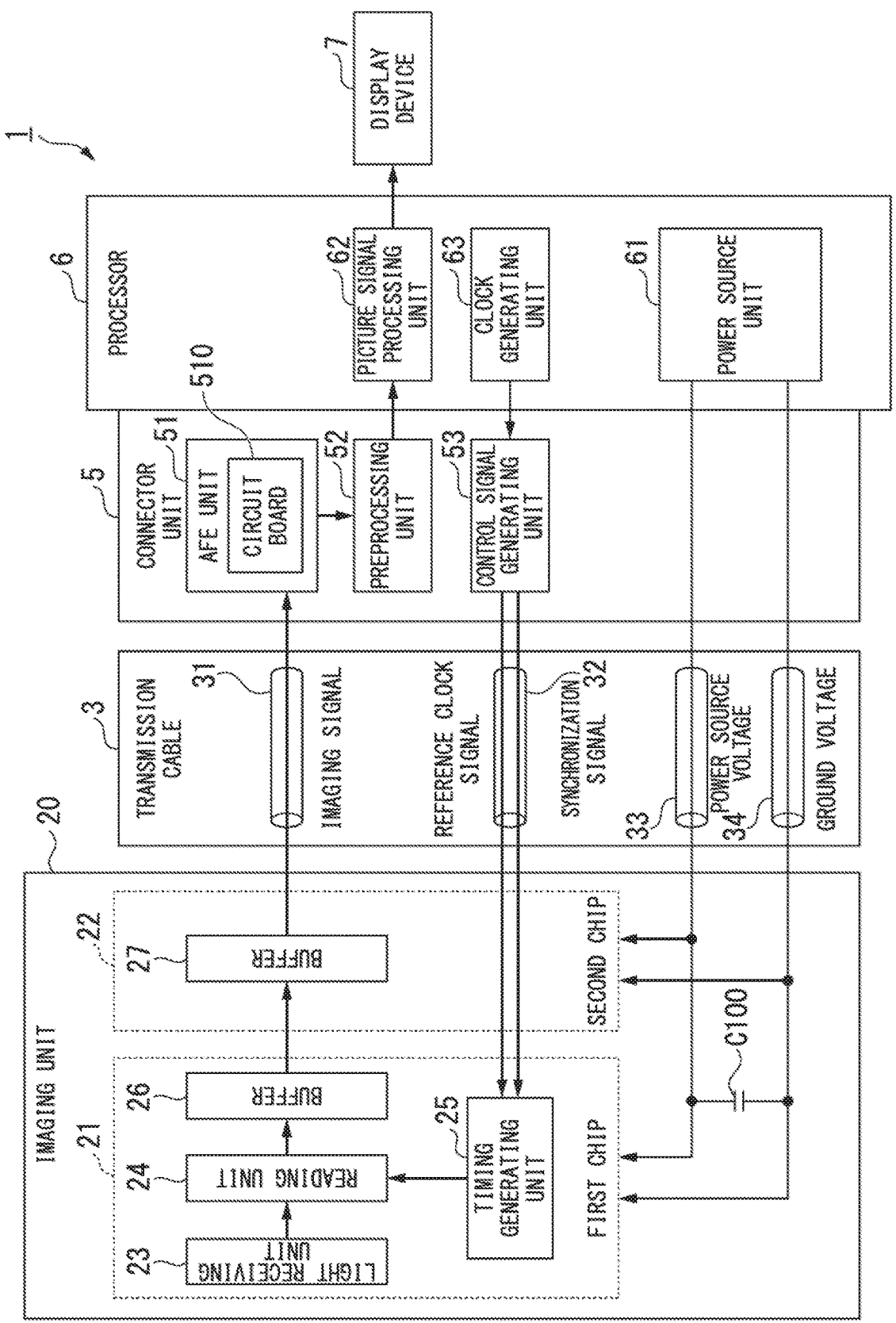
FIG. 2 is a block diagram showing the constitution of the endoscope system according to the first embodiment of the present invention.

The scope 2 has an insertion portion 70 which is inserted into a subject. The insertion portion 70 is a part of the transmission cable 3. The insertion portion 70 is inserted into the subject. The scope 2 generates an imaging signal (image data) by taking an image inside the subject. The scope 2 outputs the generated imaging signal to the processor 6. An imaging unit 20 shown in FIG. 2 is disposed at a distal end 71 of the insertion portion 70. In the insertion portion 70, the operation unit 4 is connected to an end thereof on the side opposite to the distal end 71. The operation unit 4 receives various operations on the scope 2.

The transmission cable 3 connects the imaging unit 20 of the scope 2 and the connector unit 5. The imaging signal generated by the imaging unit 20 is output to the connector unit 5 via the transmission cable 3.

The connector unit 5 is connected to the scope 2 and the processor 6. The connector unit 5 performs a predetermined signal processing on the imaging signal output from the scope 2. Further, the connector unit 5 performs an A/D conversion of an analog imaging signal into a digital signal. The connector unit 5 outputs an imaging signal which is a digital signal to the processor 6.

The processor 6 performs a predetermined image processing on the imaging signal output from the connector unit 5 and generates a picture signal. Also, the processor 6 totally controls the entire endoscope system 1.

The display device 7 displays an image corresponding to the picture signal processed by the processor 6. Further, the display device 7 displays a variety of information on the endoscope system 1.

The endoscope system 1 has a light source device which generates illumination light to be irradiated on a subject. In FIG. 1, the light source device is omitted.

FIG. 2 shows an internal constitution of the endoscope system 1. As shown in FIG. 2, the endoscope system 1 includes the imaging unit 20, the transmission cable 3, the connector unit 5, and the processor 6.

The imaging unit 20 has a first chip 21 and a second chip 22. The first chip 21 includes a light receiving unit 23, a reading unit 24, a timing generating unit 25, and a buffer 26. The imaging unit 20 serves as an imaging element. The imaging unit 20 outputs an imaging signal. The imaging unit 20 includes the light receiving unit 23 in which a plurality of pixels outputting a first voltage are disposed. The first voltage is a voltage of the imaging signal.

The light receiving unit 23 has the plurality of pixels and generates the imaging signal based on incident light. The reading unit 24 reads the imaging signal generated by the light receiving unit 23. Also, the reading unit 24 generates a reference signal. The timing generating unit 25 generates a timing signal on the basis of a reference clock signal and a synchronization signal output from the connector unit 5. The timing signal generated by the timing generating unit 25 is output to the reading unit 24. The reading unit 24 reads the imaging signal according to the timing signal. The buffer 26 temporarily holds the imaging signal read out from the light receiving unit 23 and temporarily holds the reference signal. The first chip 21 outputs the imaging signal from the buffer 26.

The second chip 22 has a buffer 27. The buffer 27 outputs the imaging signal output from the first chip 21 to the connector unit 5 via the transmission cable 3. The imaging signal is input to the buffer 27 as an input signal VIN. A combination of circuits mounted on the first chip 21 and the second chip 22 can be appropriately changed according to the design. In the endoscope system 1 shown in FIG. 1, the buffer 27 is disposed inside the imaging unit 20. The buffer 27 may be disposed inside the scope 2 and outside the imaging unit 20. As described above, the scope 2 has the imaging unit 20 and the buffer 27.

A power source voltage generated by the processor 6 and a ground voltage are transmitted to the imaging unit 20 by the transmission cable 3. In the imaging unit 20, a power supply stabilizing capacitor C100 is disposed between a signal line which transmits the power source voltage and a signal line which transmits the ground voltage.

The connector unit 5 includes an analog-front-end unit 51 (hereinafter referred to as an AFE unit 51), a preprocessing unit 52, and a control signal generating unit 53. The connector unit 5 electrically connects the scope 2 (imaging unit 20) and the processor 6. The connector unit 5 and the imaging unit 20 are connected by the transmission cable 3. The connector unit 5 and the processor 6 are connected by a coil cable.

The AFE unit 51 (imaging signal processing circuit) calculates a difference between the reference signal and the imaging signal. Further, the AFE unit 51 performs an A/D conversion of the imaging signal based on the difference. The AFE unit 51 outputs the imaging signal converted into the digital signal by the A/D conversion to the preprocessing unit 52. The AFE unit 51 includes a circuit board 510. The circuit board 510 includes a circuit which processes the imaging signal. A constitution of the circuit board 510 will be described later.

The preprocessing unit 52 performs a predetermined signal processing such as vertical line removal and noise removal on the digital imaging signal output from the AFE unit 51. The preprocessing unit 52 outputs the imaging signal subjected to the signal processing to the processor 6.

The reference clock signal serving as a reference for an operation of each portion of the scope 2 is supplied from the processor 6 to the control signal generating unit 53. For example, a frequency of the reference clock signal is 27 MHz. The control signal generating unit 53 generates a synchronization signal indicating a start position of each frame on the basis of the reference clock signal. The control signal generating unit 53 outputs the reference clock signal and the synchronization signal to the timing generating unit 25 of the imaging unit 20 via the transmission cable 3. The synchronization signal generated by the control signal generating unit 53 includes a horizontal synchronization signal and a vertical synchronization signal.

The processor 6 is a control device which totally controls the entire endoscope system 1. The processor 6 includes a power source unit 61, a picture signal processing unit 62, and a clock generating unit 63.

The power source unit 61 generates the power source voltage. The power source unit 61 outputs the power source voltage and the ground voltage to the imaging unit 20 via the connector unit 5 and the transmission cable 3.

The picture signal processing unit 62 (picture signal generating circuit) performs a predetermined image processing on the digital imaging signal processed by the preprocessing unit 52. The predetermined image processing includes a synchronizing processing, a white balance (WB) adjusting processing, a gain adjusting processing, a gamma correction processing, a digital analog (D/A) converting processing, a format converting processing, and so on. The picture signal processing unit 62 converts the imaging signal into a picture signal by this image processing. That is, the picture signal processing unit 62 processes the imaging signal (difference signal) based on the difference calculated by the AFE unit 51 and generates the picture signal based on the imaging signal. The picture signal processing unit 62 outputs the generated picture signal to the display device 7.

The clock generating unit 63 generates a reference clock signal which is a reference for an operation of each portion of the endoscope system 1. The clock generating unit 63 outputs the generated reference clock signal to the control signal generating unit 53.

The display device 7 displays an image captured by the imaging unit 20 on the basis of the picture signal output from the picture signal processing unit 62. The display device 7 has a display panel such as liquid crystal or organic electro luminescence (EL).

The transmission cable 3 has a cable 31 (first coaxial cable), a cable 32, a cable 33 (second coaxial cable), and a cable 34. The cable 31 transmits the imaging signal output from the imaging unit 20 to the connector unit 5. The cable 32 transmits a driving signal including the reference clock signal and the synchronization signal output from the control signal generating unit 53 to the imaging unit 20. The cable 33 transmits the power source voltage output from the power source unit 61 to the imaging unit 20. The cable 34 transmits the ground voltage output from the power source unit 61 to the imaging unit 20.

Figure 3:
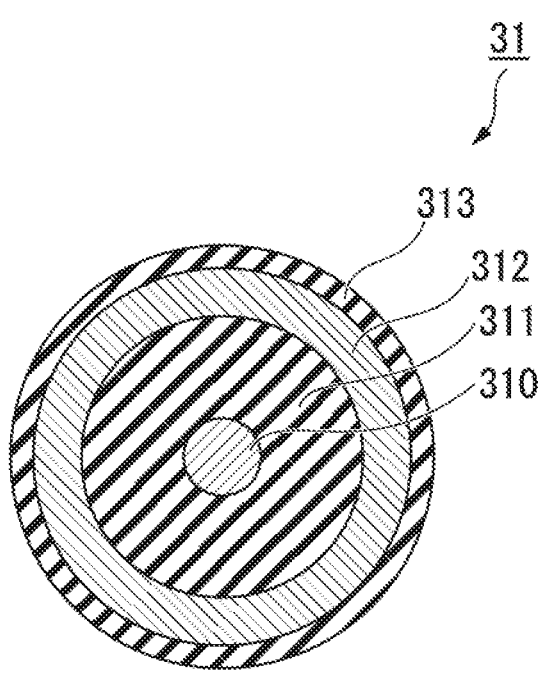
FIG. 3 is a cross-sectional view of a cable used in the endoscope system according to the first embodiment of the present invention.

The cable 31 is a coaxial cable. FIG. 3 shows a cross section of the cable 31. As shown in FIG. 3, the cable 31 has a first conductor 310, an insulator 311, a second conductor 312, and an outer sheath 313. The positions of central axes of these are the same. For example, the first conductor 310 and the second conductor 312 are formed of metal. For example, the insulator 311 and the outer sheath 313 are formed of plastic.

The first conductor 310 transmits the imaging signal output from the imaging unit 20. The insulator 311 is disposed outside the first conductor 310 and also covers (surround) the first conductor 310. The second conductor 312 is disposed outside the insulator 311 and also covers (surrounds) the insulator 311. The outer sheath 313 is disposed outside the second conductor 312 and also covers (surrounds) the second conductor 312. The first conductor 310 and the second conductor 312 are insulated by the insulator 311. At least one of the cable 32, the cable 33 and the cable 34 may be constituted with a coaxial cable. Hereinafter, an example in which the cable 32, the cable 33 and the cable 34 are constituted with coaxial cables having the same structure as that of the cable 31 will be described.

Figure 4:
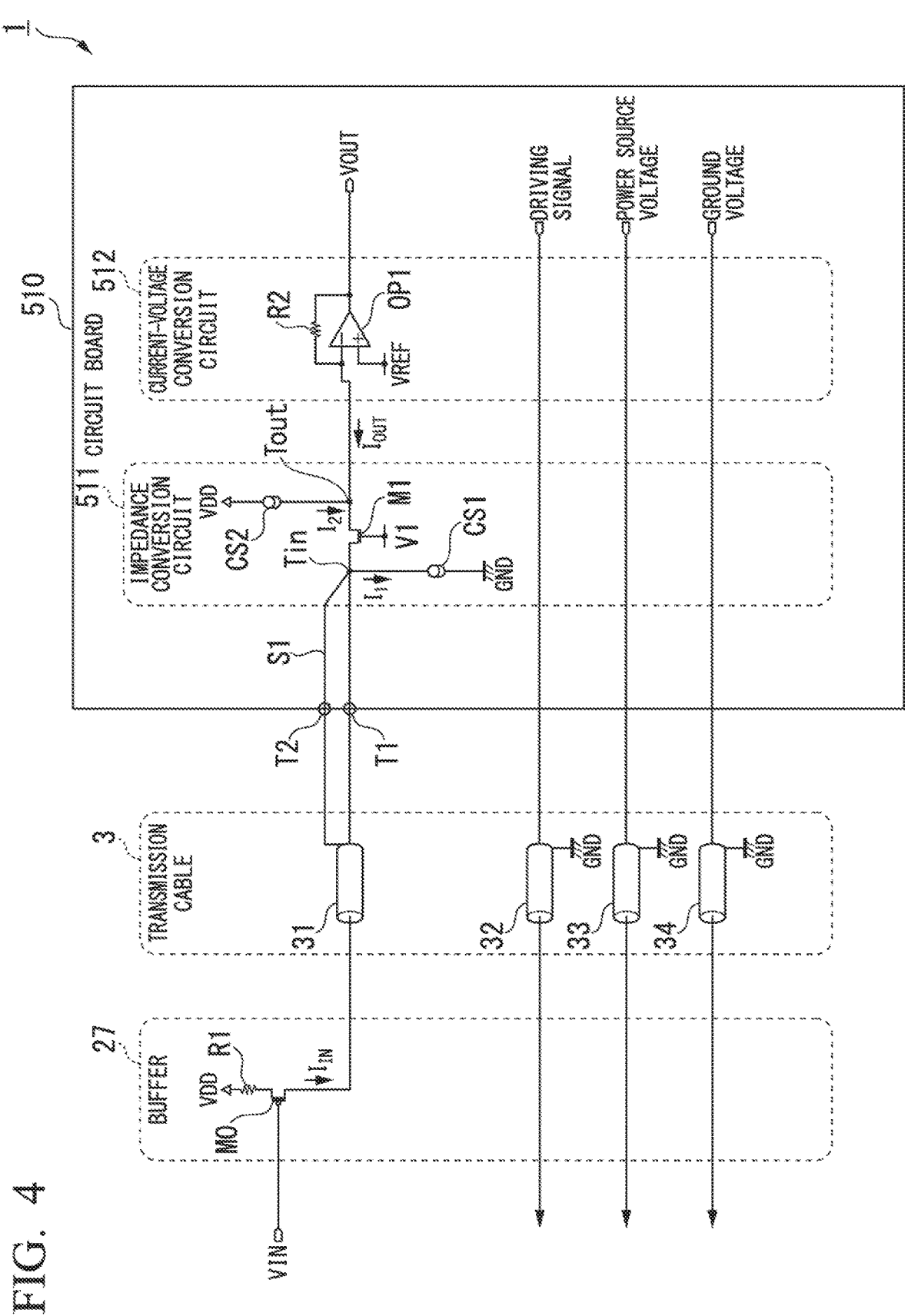
FIG. 4 is a block diagram showing a constitution of a main part of the endoscope system according to the first embodiment of the present invention.

FIG. 4 shows a constitution of a main part of the endoscope system 1. In FIG. 4, the buffer 27 (voltage-current conversion circuit), the transmission cable 3 and the circuit board 510 are shown.

The buffer 27 has a transistor M0 and a resistor R1. The resistor R1 has a first terminal and a second terminal. The first terminal of the resistor R1 is connected to a power source VDD. The transistor M0 is a PMOS transistor. The transistor M0 has a source terminal, a drain terminal and a gate terminal. The source terminal of the transistor M0 is connected to the second terminal of the resistor R1. The drain terminal of the transistor M0 is connected to the cable 31 of the transmission cable 3. The input signal VIN is input to the gate terminal of the transistor M0. The input signal VIN is an imaging signal generated in the imaging unit 20 (first chip 21). The buffer 27 converts a first voltage of the input signal VIN into a first current on the basis of a transconductance gm of the transistor M0. A current value of the first current is $I_{IN}$.

The transmission cable 3 has the cable 31, the cable 32, the cable 33 and the cable 34. The first current output from the buffer 27 is input to a first end of the first conductor 310 in the cable 31. The cable 31 transmits the first current input to the first end of the first conductor 310. The first current transmitted by the cable 31 is output from a second end of the first conductor 310 in the cable 31.

The driving signal including the reference clock signal and the synchronization signal output from the control signal generating unit 53 is input to the first end of the first conductor in the cable 32. The cable 32 transmits the driving signal input to the first end of the first conductor. The driving signal transmitted by the cable 32 is output from a second end of the first conductor in the cable 32.

The power source voltage output from the power source unit 61 is input to the first end of the first conductor in the cable 33. The cable 33 transmits the power source voltage input to the first end of the first conductor. The power source voltage transmitted by the cable 33 is output from the second end of the first conductor in the cable 33.

The ground voltage output from the power source unit 61 is input to the first end of the first conductor in the cable 34. The cable 34 transmits the ground voltage input to the first end of the first conductor. The ground voltage transmitted by the cable 34 is output from the second end of the first conductor in the cable 34.

In the cable 32, the cable 33 and the cable 34, the second conductor is connected to a ground GND. Therefore, an influence of noise due to disturbance on the signal transmitted through each cable is reduced.

The circuit board 510 has a first terminal T1, a second terminal T2 and an impedance conversion circuit 511. The first terminal T1 is connected to the first conductor 310 of the cable 31. The second terminal T2 is connected to the second conductor 312 of the cable 31.

The first current generated by the buffer 27 is input to the impedance conversion circuit 511. The impedance conversion circuit 511 outputs a second current according to the first current. The impedance conversion circuit 511 includes a transistor M1, a current source CS1 and a current source CS2.

The transistor M1 is an NMOS transistor. The transistor M1 is a gate-grounded transistor. The transistor M1 has a source terminal, a drain terminal and a gate terminal. The source terminal of the transistor M1 is connected to an input terminal Tin. The drain terminal of the transistor M1 is connected to an output terminal Tout. The gate terminal of the transistor M1 is connected to a power source V1.

The current source CS1 has a first terminal and a second terminal. The first terminal of the current source CS1 is connected to the input terminal Tin. The second terminal of the current source CS1 is connected to the ground GND. The current source CS1 is a constant current source. A current value of the current output from the current source CS1 is $I_1$. The current source CS2 has a first terminal and a second terminal. The first terminal of the current source CS2 is connected to the power source VDD. The second terminal of the current source CS2 is connected to the output terminal Tout. The current source CS2 is a constant current source. A current value of the current output from the current source CS2 is $I_2$. Between the power source VDD and the ground GND, the current source CS1, the transistor M1 and the current source CS2 are connected in series.

The input terminal Tin is electrically connected to the first terminal T1. The first current generated by the buffer 27 is input to the input terminal Tin. The first current is input to the source terminal of the transistor M1 via the input terminal Tin. A sum of the current value $I_{IN}$ input to the impedance conversion circuit 511, the current value $I_2$ flowing in the current source CS2 and the current value $I_{OUT}$ output from the output terminal Tout is the same as the current value $I_1$ flowing through the current source CS1. That is, the following Equation (1) is satisfied. In FIG. 4, a direction of the current output from the output terminal Tout is set to a direction in which the current value input to the output terminal Tout becomes positive. The current value $I_{IN}$ and the current value $I_{OUT}$ are different from each other.

$$I_{IN}+I_2+I_{OUT}=I_1 \tag{1}$$

The impedance conversion circuit 511 outputs the second current, a current value of which is $I_{OUT}$, from the output terminal Tout. The impedance conversion circuit 511 is a current conversion circuit having a low input impedance and a high output impedance. Since the impedance conversion circuit 511 outputs the second current obtained by converting the first current, a design of a current-voltage conversion circuit 512 becomes easy.

The circuit board 510 has a signal line S1. A first end of the signal line S1 is connected to the input terminal Tin. A second end of the signal line S1 is connected to the second terminal T2. The input terminal Tin is electrically connected to the second terminal T2 through the signal line S1. A second voltage according to the first current input to the input terminal Tin is output from the second terminal T2. The second terminal T2 is electrically connected to the second conductor 312 of the cable 31. Therefore, the second voltage output from the second terminal T2 is input to the second conductor 312 of the cable 31. The voltage of the first conductor 310 of the cable 31 and the voltage of the second conductor 312 are substantially the same.

The voltage of the first conductor 310 of the cable 31 changes according to a change in the first current. When the second conductor 312 of the cable 31 is connected to the ground GND, a parasitic capacitance between the first conductor 310 and the second conductor 312 is charged and discharged according to a change in the voltage of the first conductor 310 of the cable 31. Therefore, the parasitic capacitance between the first conductor 310 and the second conductor 312 becomes a load of the impedance conversion circuit 511. When a transconductance of the transistor M1 is small, it takes a longer time to charge and discharge the parasitic capacitance. When the transconductance of the transistor M1 is large, the time required for charging and discharging the parasitic capacitance is shortened. However, the noise of the current generated by the transistor M1 increases.

In the endoscope system 1, the voltage of the first conductor 310 of the cable 31 and the voltage of the second conductor 312 are substantially the same. Therefore, the charging and discharging of the parasitic capacitance between the first conductor 310 and the second conductor 312 are suppressed. That is, an effect of a driven shield is obtained. As a result, the load between the first conductor 310 and the second conductor 312 is reduced. By reducing the load between the first conductor 310 and the second conductor 312, the endoscope system 1 can transmit the imaging signal at a higher speed.

The current-voltage conversion circuit 512 includes a feedback resistor R2 and an operational amplifier OP1. The feedback resistor R2 has a first terminal and a second terminal. The operational amplifier OP1 has a non-inverting input terminal, an inverting input terminal, and an output terminal. A first terminal of the feedback resistor R2 is connected to the inverting input terminal of the operational amplifier OP1. A second terminal of the feedback resistor R2 is connected to the output terminal of the operational amplifier OP1. The inverting input terminal of the operational amplifier OP1 is connected to the output terminal Tout of the impedance conversion circuit 511. The non-inverting input terminal of the operational amplifier OP1 is connected to a power source that outputs a reference voltage VREF.

The second current output from the impedance conversion circuit 511 is input to the current-voltage conversion circuit 512. The current-voltage conversion circuit 512 converts the second current output from the impedance conversion circuit 511 into a third voltage. The current-voltage conversion circuit 512 outputs the third voltage as an output signal VOUT from an output terminal of the operational amplifier OP1.

A voltage value $V_{OUT}$ of the output signal VOUT is expressed by Equation (2). In Equation (2), $V_{REF}$ is a voltage value of the reference voltage of the current-voltage conversion circuit 512. In Equation (2), R is a resistance value of the feedback resistor R2.

$$V_{OUT}=V_{REF}+R \times I_{OUT} \tag{2}$$

As described above, the impedance conversion circuit 511 and the current-voltage conversion circuit 512 are disposed on the circuit board 510. A circuit for calculating a difference between the reference signal and the imaging signal is disposed at a subsequent stage of the circuit board 510. The circuit board 510 may be formed separately from the AFE unit 51 and may be disposed at a preceding stage of the AFE unit 51.

When the first current is transmitted in an ideal current mode by the coaxial cable and also the transmitted first current is directly input to the current-voltage conversion circuit 512, the voltage of the inverting input terminal of the operational amplifier OP1 is kept substantially constant. Therefore, it is not necessary for the second voltage according to the first current to be input to the second conductor 312. However, the first current is input to the impedance conversion circuit 511, and the input impedance of the impedance conversion circuit 511 is not zero. Accordingly, the voltage of the input terminal Tin changes due to the change of the first current. To reduce an influence of charging and discharging of the parasitic capacitance due to this voltage change, the second voltage according to the first current input to the input terminal Tin is input to the second conductor 312 of the cable 31.

A conductivity type of each transistor used for the buffer 27 and the impedance conversion circuit 511 may be opposite to the above-described conductivity type. In the buffer 27 and the impedance conversion circuit 511, although metal oxide semiconductor (MOS) transistors are used, bipolar transistors may be used.

The endoscope system according to each aspect of the present invention need not have the constitution corresponding to at least one of the operation unit 4, the processor 6 and the display device 7. The endoscope system according to each aspect of the present invention need not have the constitution corresponding to at least one of the preprocessing unit 52 and the control signal generating unit 53. The endoscope system according to each aspect of the present invention need not have the constitution corresponding to at least one of the cable 32, the cable 33 and the cable 34. The endoscope system according to each aspect of the present invention need not have the current-voltage conversion circuit 512.

The imaging signal is not limited to an analog signal. The imaging signal may be a digital signal. When the imaging signal is a digital signal, the connector unit 5 includes a circuit such as a comparator capable of detecting a High/Low voltage instead of the AFE unit 51.

As described above, the endoscope system 1 includes the imaging unit 20 (imaging element), the buffer 27 (voltage-current conversion circuit), the cable 31 (first coaxial cable) and the impedance conversion circuit 511. The imaging unit 20 generates the first voltage (imaging signal). The buffer 27 is disposed inside or outside the imaging unit 20 and converts the first voltage into the first current. The cable 31 has the first conductor 310 and the second conductor 312. The second conductor 312 is disposed outside the first conductor 310. The first current is transmitted through the first conductor 310. The first current transmitted by the first conductor 310 is input to the impedance conversion circuit 511. The impedance conversion circuit 511 outputs a second current according to the first current. The second voltage according to the first current is input to the second conductor 312.

In the first embodiment, the second voltage according to the first current is input to the second conductor 312. Therefore, the endoscope system 1 can transmit a signal from the imaging unit 20 at a higher speed.

The endoscope system 1 may include the cable 33 (second coaxial cable) which transmits a power source voltage supplied to the imaging unit 20 (imaging element). By inputting the second voltage according to the first current into the second conductor 312, the parasitic capacitance is formed between the second conductor 312 and the cable 33. Due to the change in the second voltage, noise may be transmitted to the cable 33 via the parasitic capacitance. Since the cable 33 is constituted with a coaxial cable, it is difficult for the noise to be transmitted to the power source voltage transmitted through the cable 33. The cable 32 and the cable 34 are also formed of coaxial cables. Accordingly, it is difficult for the noise to be transmitted to the drive signal transmitted through the cable 32 and the ground voltage transmitted through the cable 34.

Modified Example of First Embodiment

Figure 5:
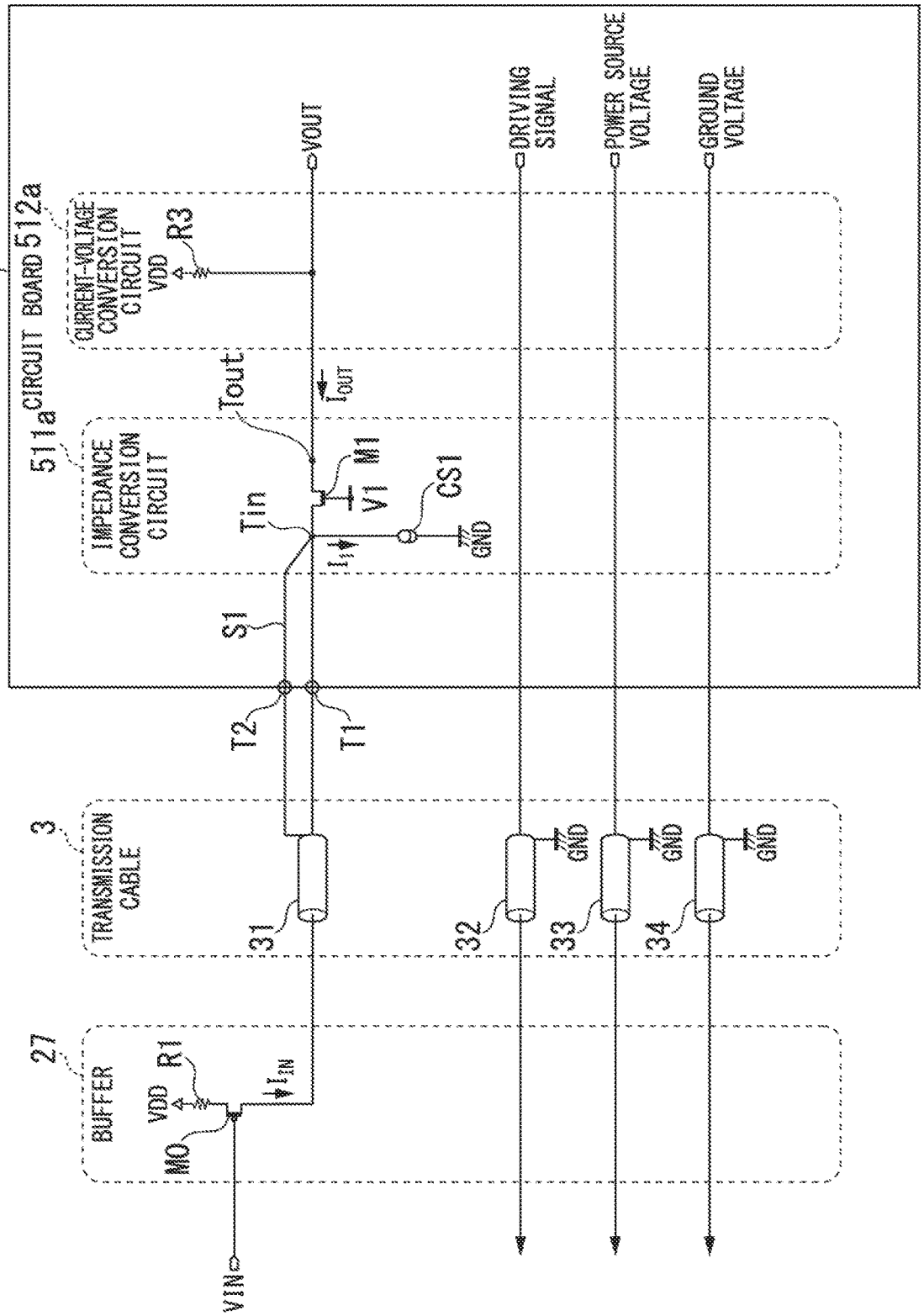
FIG. 5 is a block diagram showing a constitution of a main part of an endoscope system according to a modified example of the first embodiment of the present invention.

FIG. 5 shows a constitution of a main part of the endoscope system 1a according to a modified example of the first embodiment. In FIG. 5, a buffer 27 (voltage-current conversion circuit), a transmission cable 3 and a circuit board 510a are shown. With respect to the constitution shown in FIG. 5, points different from the constitution shown in FIG. 4 will be described.

The circuit board 510 shown in FIG. 4 is changed to the circuit board 510a shown in FIG. 5. In the circuit board 510a, the impedance conversion circuit 511 shown in FIG. 4 is changed to an impedance conversion circuit 511a, and the current-voltage conversion circuit 512 shown in FIG. 4 is changed to a current-voltage conversion circuit 512a.

In the impedance conversion circuit 511a, the current source CS2 in the impedance conversion circuit 511 is deleted.

The current-voltage conversion circuit 512a has a resistor R3. The resistor R3 has a first terminal and a second terminal. The first terminal of the resistor R3 is connected to an output terminal Tout of the impedance conversion circuit 511a. The second terminal of the resistor R3 is connected to a power source VDD.

A second current output from the impedance conversion circuit 511a is input to the current-voltage conversion circuit 512a. The current-voltage conversion circuit 512a converts the second current into a third voltage and outputs the third voltage as an output signal VOUT from the first terminal of the resistor R3.

Regarding points other than the above, the constitution shown in FIG. 5 is the same as the constitution shown in FIG. 4. Constitutions other than the constitution shown in FIG. 5 are the same as those which have already been described.

The impedance conversion circuit 511 shown in FIG. 4 and the current-voltage conversion circuit 512a shown in FIG. 5 may be disposed on the circuit board. The impedance conversion circuit 511a shown in FIG. 5 and the current-voltage conversion circuit 512 shown in FIG. 4 may be disposed on the circuit board.

Second Embodiment

Figure 6:
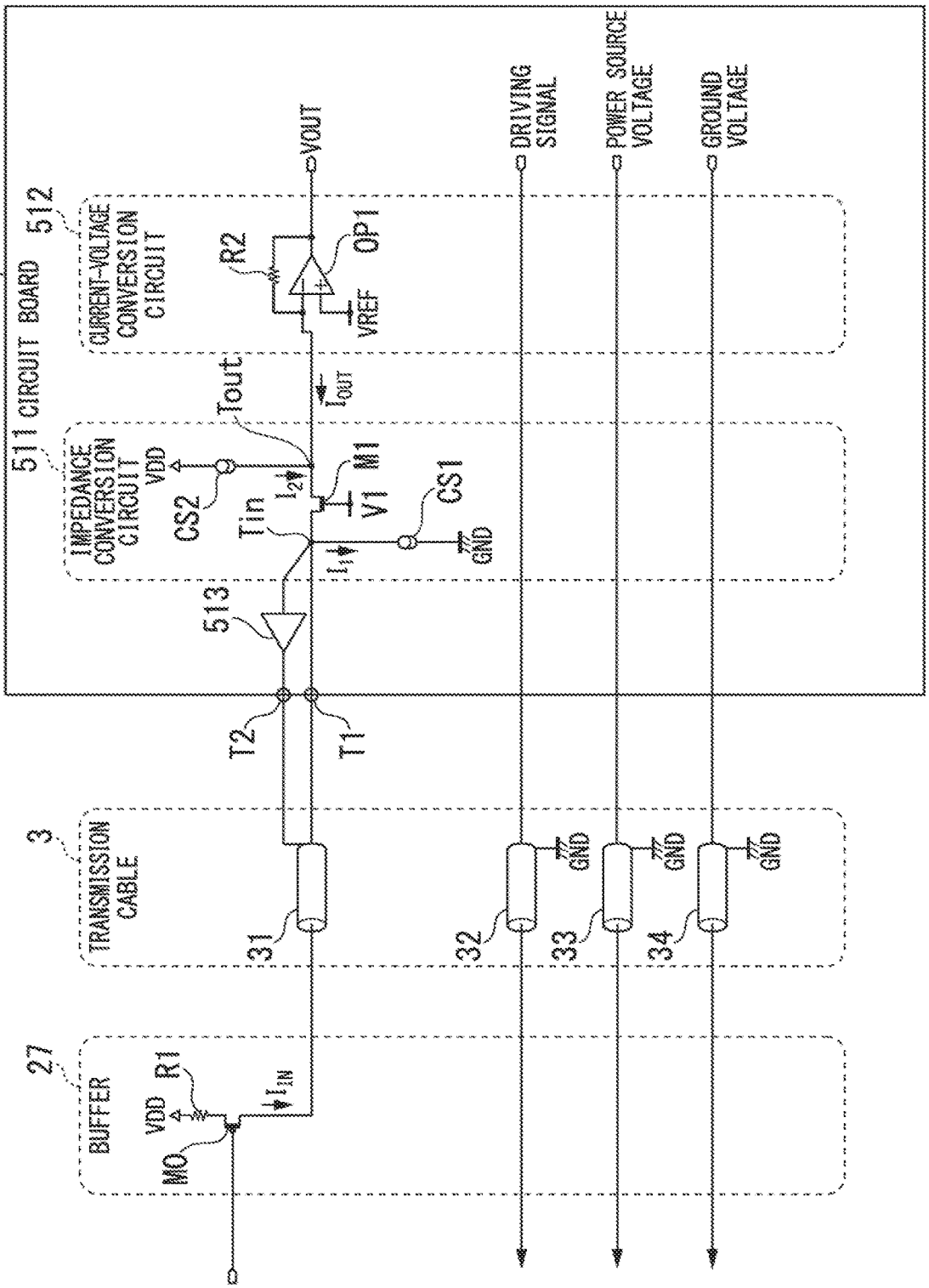
FIG. 6 is a block diagram showing a constitution of a main part of an endoscope system according to a second embodiment of the present invention.

FIG. 6 shows the constitution of a main part of an endoscope system 1b of a second embodiment. In FIG. 6, a buffer 27 (voltage-current conversion circuit), a transmission cable 3 and a circuit board 510b are shown. In the constitution shown in FIG. 6, points different from the constitution shown in FIG. 4 will be described.

The circuit board 510 shown in FIG. 4 is changed to a circuit board 510b shown in FIG. 6. The circuit board 510b includes an impedance conversion circuit 511, a current-voltage conversion circuit 512 and a buffer 513.

The buffer 513 has an input terminal and an output terminal. The input terminal of the buffer 513 is connected to an input terminal Tin of the impedance conversion circuit 511. Therefore, the second voltage according to the first current is input to the buffer 513. The output terminal of the buffer 513 is connected to a second terminal T2. Therefore, the buffer 513 outputs the second voltage to the second terminal T2.

For example, the buffer 513 is a voltage follower. The buffer 513 may be a source follower using a MOS transistor. The buffer 513 may be an emitter follower using a bipolar transistor. The buffer 513 may be a circuit other than these circuits. It is relatively easy to reduce an output impedance of the buffer 513. Therefore, a shielding effect against the noise due to disturbance can be sufficiently secured.

Regarding points other than the above, the constitution shown in FIG. 6 is the same as the constitution shown in FIG. 4. Constitutions other than the constitution shown in FIG. 6 are the same as those which have already been described. The circuit board 510a shown in FIG. 5 may have the buffer 513.

As described above, the endoscope system 1b has the buffer 513 which outputs the second voltage according to the first current. By disposing the buffer 513 having a driving capability, the transconductance of the transistor M1 can be reduced.

The circuit board 510 in the first embodiment has the first terminal T1 and the second terminal T2. The first current transmitted by the first conductor 310 of the cable 31 is input to the first terminal T1. The first terminal T1 is electrically connected to the impedance conversion circuit 511. The second terminal T2 is electrically connected to the impedance conversion circuit 511 and also outputs the second voltage.

By providing the first terminal T1 and the second terminal T2, it becomes easy to insert the buffer 513 between the input terminal Tin and the second terminal T2 of the impedance conversion circuit 511.

Third Embodiment

Figure 7:
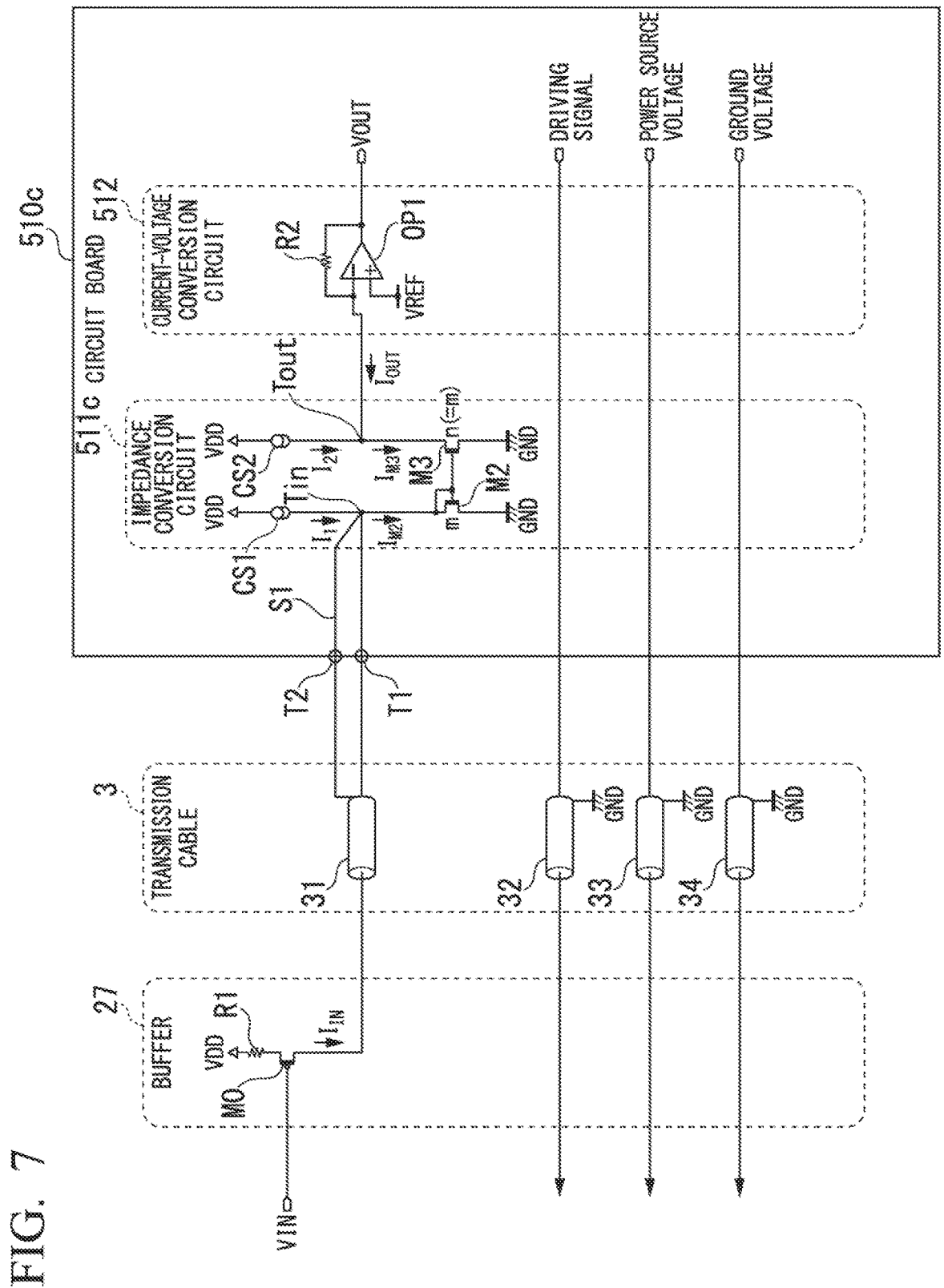
FIG. 7 is a block diagram showing a constitution of a main part of an endoscope system according to a third embodiment of the present invention.

FIG. 7 shows a constitution of the main part of an endoscope system 1c according to a third embodiment. In FIG. 7, a buffer 27 (voltage-current conversion circuit), a transmission cable 3 and a circuit board 510c are shown. Regarding the constitution shown in FIG. 7, points different from the constitution shown in FIG. 4 will be described.

The circuit board 510 shown in FIG. 4 is changed to a circuit board 510c shown in FIG. 7. In the circuit board 510c, the impedance conversion circuit 511 shown in FIG. 4 is changed to an impedance conversion circuit 511c.

The impedance conversion circuit 511c includes a current source CS1, a current source CS2, a transistor M2 and a transistor M3.

The current source CS1 has a first terminal and a second terminal. The first terminal of the current source CS1 is connected to the power source VDD. The second terminal of the current source CS1 is connected to the input terminal Tin. The current source CS1 is a constant current source. A current value of a current output from the current source CS1 is $I_1$. The current source CS2 has a first terminal and a second terminal. The first terminal of the current source CS2 is connected to the power source VDD. The second terminal of the current source CS2 is connected to the output terminal Tout. The current source CS2 is a constant current source. A current value of a current output from the current source CS2 is $I_2$.

The transistor M2 and the transistor M3 constitute a current mirror. The transistors M2 and M3 are NMOS transistors. The transistor M2 and the transistor M3 have a source terminal, a drain terminal and a gate terminal. The drain terminal of the transistor M2 is connected to the input terminal Tin. The source terminal of the transistor M2 is connected to the ground GND. The gate terminal of the transistor M2 is connected to the drain terminal of the transistor M2. The drain terminal of the transistor M3 is connected to the output terminal Tout. The source terminal of the transistor M3 is connected to the ground GND. The gate terminal of the transistor M3 is connected to the gate terminal of the transistor M2. The transistor M3 is connected to the current-voltage conversion circuit 512 via the output terminal Tout. Between the power source VDD and the ground GND, the current source CS1 and the transistor M2 are connected in series and the current source CS2 and the transistor M3 are also connected in series.

A first current generated by the buffer 27 is input to the input terminal Tin. The first current is input to the transistor M2 via the input terminal Tin. The first current flows between the drain terminal and the source terminal of the transistor M2. A current according to a mirror ratio between the transistor M2 and the transistor M3 flows between the drain terminal and the source terminal of the transistor M3. It is assumed that W/L ratios of the transistor M2 and the transistor M3 are the same. When a coefficient of the transistor M2 is m and a coefficient of the transistor M3 is n, the current value of the current flowing through the transistor M3 is (n/nm) times the current value of the current flowing through the transistor M2. When the coefficients of the transistor M2 and the transistor M3 are the same, the currents flowing through the transistor M2 and the transistor M3 are the same. The impedance conversion circuit 511c outputs a second current, a current value of which is $I_{OUT}$, from the output terminal Tout. The impedance conversion circuit 511c is a current conversion circuit having a low input impedance and a high output impedance.

The input terminal Tin is electrically connected to the first terminal T1. A first current generated by the buffer 27 is input to the input terminal Tin. The first current is input to the transistor M2 via the input terminal Tin. For ease of explanation, it is assumed that the mirror ratio between the transistor M2 and the transistor M3 is 1. The current value of the current flowing through the transistor M2 is $I_{M2}$. The transistor M3 outputs a current having the same current value as that of the current flowing through the transistor M2. The current value of the current flowing through the transistor M3 is $I_{M3}$.

A sum of the current value $I_{IN}$ input to the impedance conversion circuit 511c and the current value $I_1$ flowing through the current source CS1 is the same as the current value $I_{M2}$ flowing through the transistor M2. That is. Equation (3) is satisfied.

$$I_{IN} + I_1 = I_{M2} \qquad (3)$$

A sum of the current value $I_2$ flowing through the current source CS2 and the current value $I_{OUT}$ output from the output terminal Tout is the same as the current value $I_{M3}$ flowing through the transistor M3. That is, Equation (4) is satisfied. In FIG. 7, a direction of the current output from the output terminal Tout is set in a direction in which the current value input to the output terminal Tout becomes positive.

$$I_2 + I_{OUT} = I_{M3} \qquad (4)$$

Regarding points other than the above, the constitution shown in FIG. 7 is the same as the constitution shown in FIG. 4. Constitutions other than the constitution shown in FIG. 7 are the same as those which have already been described. The impedance conversion circuit 511c may have the buffer 513 shown in FIG. 6.

The conductivity type of each transistor used for the buffer 27 and the impedance conversion circuit 511c may be opposite to the above-described conductivity type. In the buffer 27 and the impedance conversion circuit 511c, although MOS transistors are used, bipolar transistors may be used.

In the third embodiment, the second voltage according to the first current is input to the second conductor 312. Therefore, the endoscope system 1c can transmit a signal from the imaging unit 20 at a higher speed.

Modified Example of Third Embodiment

Figure 8:
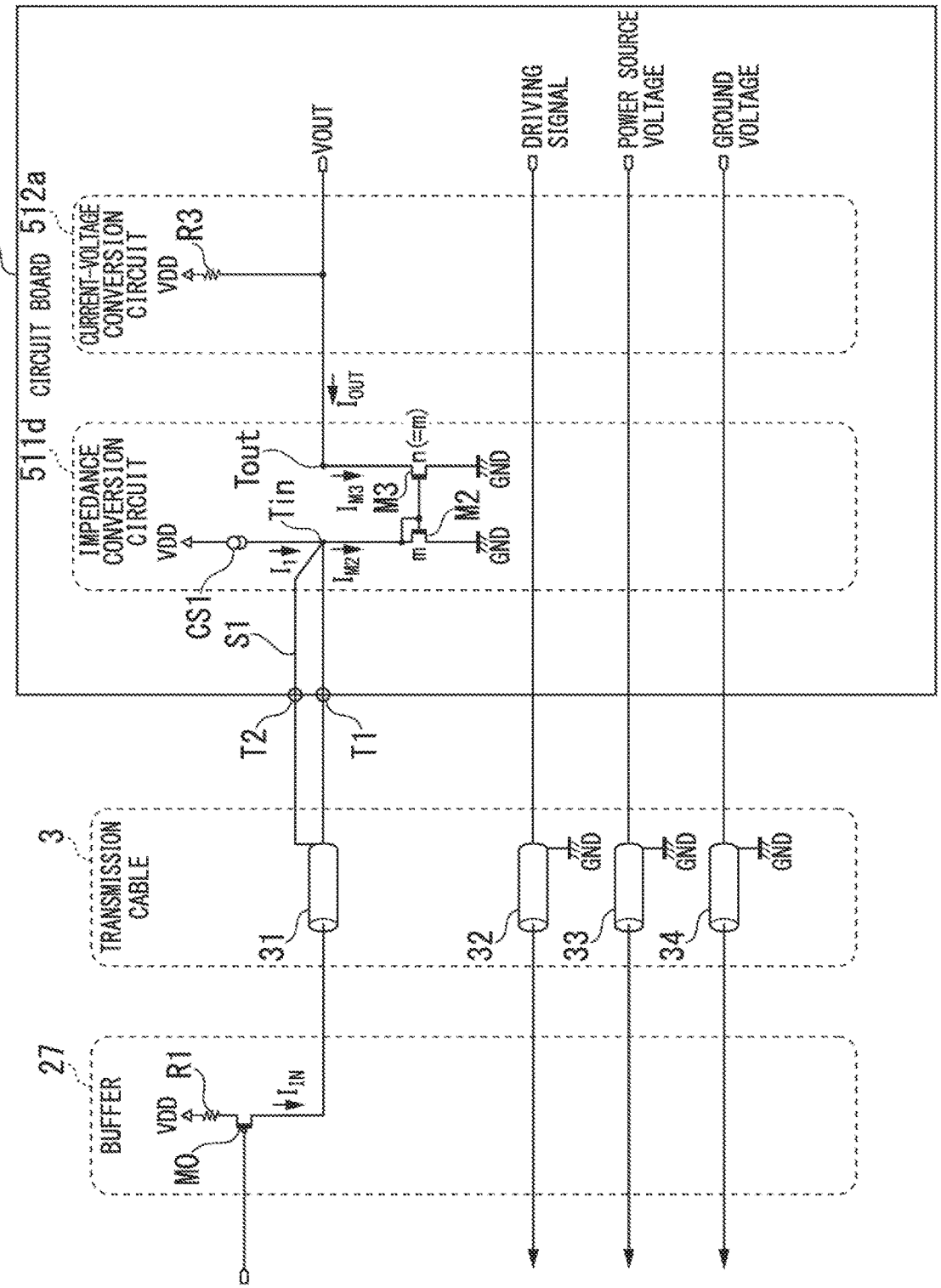
FIG. 8 is a block diagram showing a constitution of a main part of an endoscope system according to a modified example of the third embodiment of the present invention.

FIG. 8 shows a constitution of a main part of an endoscope system 1d according to a modified example of the third embodiment. In FIG. 8, a buffer 27 (voltage-current conversion circuit), a transmission cable 3 and a circuit board 510d are shown. Regarding the constitution shown in FIG. 8, points different from the configuration shown in FIG. 7 will be described.

The circuit board 510c shown in FIG. 7 is changed to a circuit board 510d shown in FIG. 8. In the circuit board 510d, the impedance conversion circuit 511c shown in FIG. 7 is changed to an impedance conversion circuit 511d, and the current-voltage conversion circuit 512 shown in FIG. 7 is changed to a current-voltage conversion circuit 512a.

In the impedance conversion circuit 511d, the current source CS2 in the impedance conversion circuit 511c is deleted. The current-voltage conversion circuit 512a is the same as the current-voltage conversion circuit 512a shown in FIG. 5. The same current as the current flowing through the transistor M3 is output as the second current from the output terminal Tout.

The second current output from the impedance conversion circuit 511d is input to the current-voltage conversion circuit 512a. The current-voltage conversion circuit 512a converts the second current into a third voltage and outputs the third voltage as an output signal VOUT from the first terminal of the resistor R3.

Regarding the points other than the above, the constitution shown in FIG. 8 is the same as the constitution shown in FIG. 7. Constitutions other than the constitution shown in FIG. 8 are the same as those which have already been described. The impedance conversion circuit 511d may have the buffer 513 shown in FIG. 6.

The impedance conversion circuit 511c shown in FIG. 7 and the current-voltage conversion circuit 512a shown in FIG. 8 may be disposed on the circuit board. The impedance conversion circuit 511d shown in FIG. 8 and the current-voltage conversion circuit 512 shown in FIG. 7 may be disposed on the circuit board.

While preferred embodiments of the invention have been described and shown above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An endoscope system, comprising:
   an imaging element configured to generate a first voltage,
   a voltage-current conversion circuit disposed inside or outside the imaging element and configured to convert the first voltage into a first current,
   a first coaxial cable having a first conductor and a second conductor, the second conductor being disposed outside the first conductor, the first current being transmitted through the first conductor,
   a current-voltage conversion circuit configured to convert the second current output from the impedance conversion circuit into a third voltage, and
   a circuit board on which the impedance conversion circuit and the current-voltage conversion circuit are disposed,
   an impedance conversion circuit to which the first current transmitted through the first conductor is input and configured to output a second current according to the first current,
   wherein a second voltage according to the first current is input to the second conductor, and
   the circuit board comprises
   a first terminal to which the first current transmitted through the first conductor is input and which is electrically connected to the impedance conversion circuit, and
   a second terminal electrically connected to the impedance conversion circuit and configured to output the second voltage.

2. The endoscope system according to claim 1, further comprising a buffer configured to output the second voltage according to the first current.

3. The endoscope system according to claim 1, further comprising a second coaxial cable configured to transmit a power source voltage supplied to the imaging element.

* * * * *